US 6,741,890 B1

(12) United States Patent
Seim et al.

(10) Patent No.: US 6,741,890 B1
(45) Date of Patent: May 25, 2004

(54) METHOD AND APPARATUS FOR DETECTION OF PREMATURE ATRIAL CONTRACTIONS

(75) Inventors: Gary T. Seim, Minneapolis, MN (US); Victor T. Chen, Minnetrista, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 272 days.

(21) Appl. No.: 09/615,488

(22) Filed: Jul. 13, 2000

(51) Int. Cl.[7] .............................................. A61N 1/362
(52) U.S. Cl. ......................................................... 607/9
(58) Field of Search .............................. 607/2, 4, 5, 6, 607/7, 14, 9, 13; 600/510

(56) References Cited

U.S. PATENT DOCUMENTS

| | | | |
|---|---|---|---|
| 4,784,153 A | 11/1988 | Marks | 128/701 |
| 4,788,980 A | 12/1988 | Mann et al. | 128/419 PG |
| 5,318,594 A | * 6/1994 | Limousin et al. | 607/9 |
| 5,403,356 A | * 4/1995 | Hill et al. | 607/14 |
| 5,713,928 A | * 2/1998 | Bonnet et al. | 607/14 |
| 5,931,857 A | 8/1999 | Prieve et al. | 607/14 |
| 5,954,755 A | 9/1999 | Casavant | 607/28 |
| 5,991,656 A | 11/1999 | Olson et al. | 607/4 |
| 6,306,087 B1 | * 10/2001 | Barnhill et al. | 128/924 |

* cited by examiner

Primary Examiner—George R. Evanisko
(74) Attorney, Agent, or Firm—Schwegman, Lundberg, Woessner & Kluth, P.A.

(57) ABSTRACT

A system and method for detecting premature atrial contractions in which a function of A—A intervals measured between successive atrial senses is computed and compared with a present A—A interval. In accordance with the invention, a premature atrial contraction is detected if the present A—A interval is less than a specified percentage of a moving average of previous A—A intervals and below a specified absolute limit value.

16 Claims, 1 Drawing Sheet

METHOD AND APPARATUS FOR DETECTION OF PREMATURE ATRIAL CONTRACTIONS

FIELD OF THE INVENTION

This invention pertains to systems and methods for the detection of cardiac arrhythmias and, in particular, for the detection of premature atrial contractions.

BACKGROUND

Two broad classes of cardiac rhythm management devices are pacemakers and implantable cardioverter/defibrillators. Cardiac pacemakers are medical devices, usually implantable, that provide electrical stimulation in the form of pacing pulses to selected chambers of the heart (i.e., the atrium and/or ventricle) in order to either make up for the heart's inability to pace itself at an appropriate rhythm in order to meet metabolic demand (bradycardia pacing) or to therapeutically treat abnormal rhythms such as tachycardias (antitachycardia pacing). Pacemakers typically have a programmable electronic controller that causes the pacing pulses to be output in response to lapsed time intervals and sensed electrical activity (i.e., intrinsic heart beats not due to a pacing pulse). Implantable pacemakers sense intrinsic cardiac electrical activity by means of internal electrodes disposed in or near the chamber to be sensed. A depolarization wave associated with an intrinsic contraction of the atria or ventricles that is detected by the pacemaker is referred to as an atrial sense (A-sense) or ventricular sense (V-sense), respectively. In order to cause a contraction in the absence of an intrinsic beat, a pacing pulse (either an atrial pace or a ventricular pace) with energy above a certain pacing threshold must be delivered to the chamber. Cardioversion and defibrillation refer to electrical shocks delivered to the heart in order to terminate a tachycardia, including atrial or ventricular fibrillation. The electric shock terminates the tachycardia by depolarizing all excitable myocardium which thereby prolongs refractoriness, interrupts reentrant circuits, and discharges excitatory foci. Implantable cardioverter/defibrillators (ICD's) provide this kind of therapy by delivering a shock pulse to the heart when fibrillation or other type of tachycardia is detected by the device.

Premature atrial contractions (PACs) are atrial contractions resulting from ectopic excitatory foci in the atria that occur prior to the time they would normally be expected. Such premature excitation of the atria spreads to the atrioventricular (AV) node and may or may not be conducted to the ventricles depending upon whether the AV node is still refractory from the preceding beat. Ectopic foci can be due to local areas of ischemia, but premature atrial contractions can also occur in normal persons when provoked by drugs, alcohol, caffeine, or tobacco. Premature atrial contractions may depress cardiac output (due to lessened diastolic filling of the ventricles) and can also precipitate other tachyarrhythmias.

One way of detecting PACs is to measure the interval between A-senses, referred to as the A—A interval, and declare an A-sense to be a PAC if the current A—A interval is less than a specified percentage of the preceding A—A interval. The problem with methods that base a PAC detection decision upon a single preceding A—A interval, however, is a lack of specificity. That is, such methods can be fooled into defining events as PACs that are not PACs. For example, some individuals exhibit occasional sinus pauses when exercising. A PAC detection method based upon a single preceding A—A interval will call every event after those pauses a PAC even though they are physiologic and normal. It is toward the objective of reducing such false positive results that the present invention is primarily directed.

SUMMARY OF THE INVENTION

The present invention is an improved system and method for detecting PACs based upon measurement of preceding A—A intervals. Atrial events corresponding to depolarizations or paces are detected with an atrial sensing channel, and corresponding A—A intervals are measured. A present A—A interval, defined as the time interval between a presently detected atrial event and a previously detected atrial event, is measured, and a moving average of such A—A intervals is computed. The A—A interval moving average is preferably computed from at least four A—A intervals. In accordance with the invention, a detected atrial depolarization is classified as a premature atrial contraction if the present A—A interval is less than a specified value based upon the A—A interval moving average, such as a specified fraction of the moving average. In a preferred embodiment, the fraction of the A—A interval moving average that the present A—A interval must be less than in order for a premature atrial contraction to be detected is set to seventy-five percent. To obtain further specificity, the method may limit the value of an A—A interval used to compute the moving average A—A interval to being no longer than a specified maximum value, such as approximately 2000 milliseconds. An additional detection criteria may be employed in which the present A—A interval is required to also be less than a specified absolute value in order for a premature atrial contraction to be detected. In an exemplary embodiment, the specified absolute value is set to approximately 600–750 milliseconds.

DETAILED DESCRIPTION OF A SPECIFIC EMBODIMENT

As noted above, the present invention overcomes some of the lack of specificity problems exhibited by prior methods of detecting PACs by basing the detection upon a moving average of preceding A—A intervals. An A—A interval is the time period between successive detected atrial events, with an atrial event defined as either an A-sense (i.e., a detected atrial depolarization or P-wave) or an A-pace (i.e., a pacing pulse delivered to the atria). Atrial events are detected by an atrial sensing channel such as is commonly included in a cardiac rhythm management device, an example of which is described more fully below. A function based upon previously detected A—A intervals is computed, and each presently detected A—A interval is compared with the A—A interval function. In a presently preferred embodiment, the A—A interval function is a moving average of the previously detected A—A intervals, and a detected atrial depolarization is classified as a PAC if the presently detected A—A interval is less than a specified value based upon the A—A interval moving average, such a specified fraction of the moving average. In a further refinement, an atrial depolarization is classified as a PAC if the A—A interval is less than a specified fraction of the A—A interval moving average and is also less than a specified absolute value.

Figure 1:
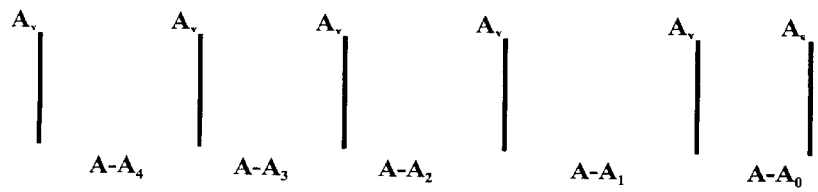
FIG. 1 is an illustration of detected A—A intervals.

FIG. 1 is a depiction of detected atrial events A, in time sequence, where the atrial events can either be an atrial pace $A_p$ or an atrial sense $A_s$. The time interval between each successive atrial event is designated A–$A_n$, where n=0 for the present A—A interval, n=1 for the immediately preceding A—A interval, n=2 for the next preceding interval, and so on. A moving average of preceding A—A intervals, designated A–$A_{avg}(t)$, can be computed as:

$$(A-A_{avg}(t))=(A-A_1+A-A_2+A-A_3+\ldots A-A_n)/n$$

In a preferred embodiment, n is at least four so that the moving average is based upon the four preceding A—A intervals. In order to prevent the moving average from being corrupted due to undersensing of atrial events, the method may limit the value of an A—A interval used to compute the moving average A—A interval to being no longer than a specified maximum value, such as approximately 2000 milliseconds.

In accordance with the invention, an atrial sense is classified as a PAC if the present A—A interval is less than a specified value based upon the moving average of preceding A—A intervals. That is, if:

$$A-A_0 < f(A-A_{avg}(t))$$

where $f(A-A_{avg}(t))$ is a function of the moving average, such as a specified fractional amount. In a preferred embodiment, the specified fractional amount is approximately seventy-five percent. Additional specificity is obtained by additionally requiring that the present A—A interval also be less than a specified absolute value before an atrial sense is classified as a PAC. This absolute value is preferably set to approximately 600 milliseconds. The requirement for the detection of a PAC is then:

$$A\text{-}A_0<(0.75)(A-A_{avg}(t)) \text{ AND } A-A_0<600$$

Figure 2:
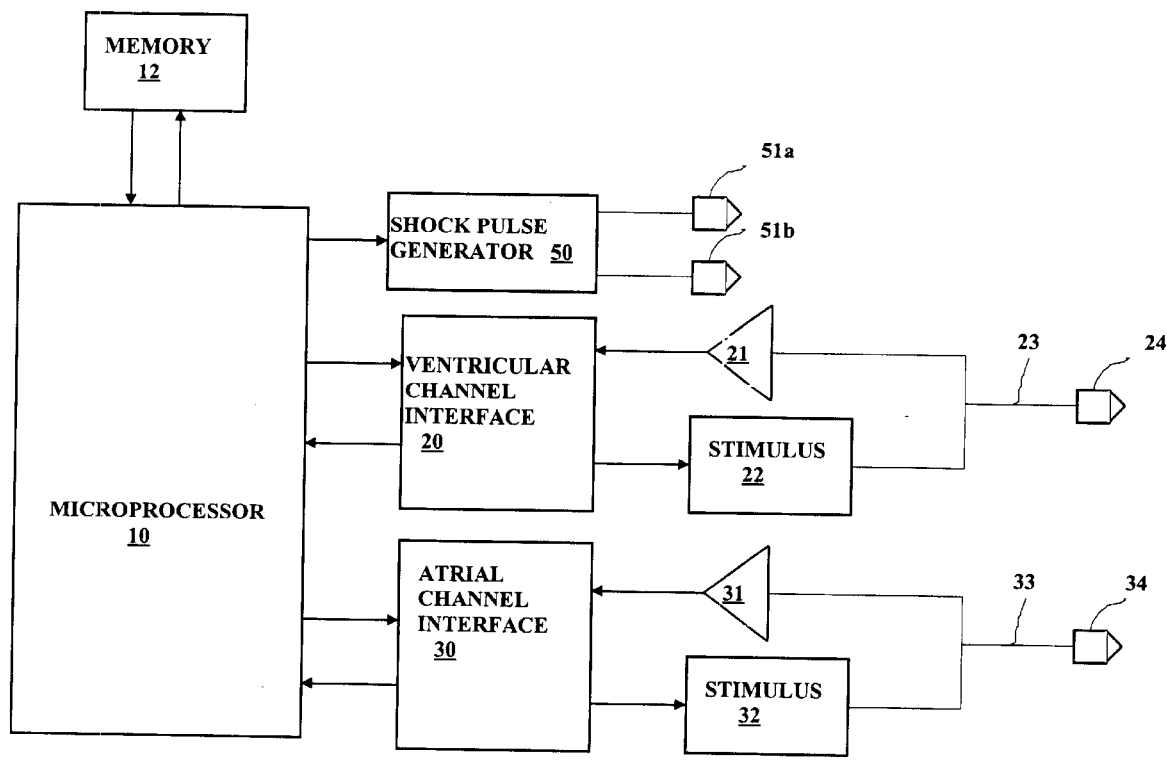
FIG. 2 is a system diagram of a cardiac rhythm management device.

FIG. 2 is a system diagram of a microprocessor-based cardiac rhythm management device, which in this case is an implantable cardioverter/defibrillator (ICD) with the capability of also delivering pacing therapy. Such a device is capable of conventional bradycardia or tachycardia pacing as well as arrhythmia termination by a shock pulse. The controller in this device is a microprocessor 10 that controls the output of pacing pulses and shock pulses in accordance with sensed cardiac electrical activity and lapsed time intervals. The microprocessor 10 communicates with a memory 12 via a bidirectional data bus. The memory 12 typically comprises a ROM or RAM for program storage and a RAM for data storage. The device has atrial sensing and pacing channels comprising electrode 34, lead 33, sensing amplifier 31, pulse generator 32, and an atrial channel interface 30 which communicates bidirectionally with a port of microprocessor 10. The ventricular sensing and pacing channels similarly comprise electrode 24, lead 23, sensing amplifier 21, pulse generator 22, and a ventricular channel interface 20. The sensing channels sense cardiac electrical activity from an electrode placed in proximity to a particular region of the heart and produce a sense signal in accordance therewith. A shock pulse generator 50 is also interfaced to the microprocessor for delivering cardioversion or defibrillation pulses to the heart via a pair of terminals 51a and 51b that are connected by defibrillation leads to shock electrodes placed in proximity to regions of the heart. For each channel, the same lead and electrode are used for both sensing and pacing.

Detection of PACs provides a useful function in cardiac rhythm management devices such as that illustrated in FIG. 1. The PAC detection method as described above is implemented in the form of instructions in memory executed by the microprocessor 10, with the time intervals between A-senses detected by the atrial sensing channel measured by either hardware or software timers. For example, the device may incorporate an arrhythmia prediction scheme utilizing PAC detection and possibly deliver some kind of anti-tachycardia therapy accordingly after detection of one or more PACs. PAC detection may also be employed in a bradycardia pacemaker in which PACs are distinguished from normal A-senses for timing purposes. For example, if a PAC is detected that is not conducted to the ventricles, the atrial escape interval may be timed from the previous normal A-sense and not from the PAC. In another example, a pacemaker operating in an atrial tracking pacing mode (e.g., DDD or VDD) may be programmed after detection of a PAC to deliver an atrial pace with a longer or shorter atrial escape interval so as to avoid competitive pacing or to simply revert to a non-atrial tracking pacing mode. The present invention can be used to advantage by the device in either its pacemaker or arrhythmia treatment/prevention capacity, and can be used in conjunction with other methods of beat/arrhythmia detection.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A method for detecting premature atrial contractions, comprising:

detecting atrial events corresponding to atrial depolarizations or paces;

measuring a present A—A interval defined as the time interval between a presently detected atrial event and a previously detected atrial event;

computing a function based upon a plurality of measured A—A intervals;

detecting a premature atrial contraction if the present A—A interval is less than the computed A—A interval function and wherein the present A—A interval must also be less than a specified absolute value in order for a premature atrial contraction to be detected.

2. The method of claim 1 wherein the A—A interval function is a moving average of A—A intervals, and further comprising detecting a premature atrial contraction if the present A—A interval is less than a specified value based upon the A—A interval moving average.

3. The method of claim 2 wherein the specified value based upon the A—A interval moving average is a specified fraction of the A—A interval moving average.

4. The method of claim 3 wherein the specified fraction is approximately seventy-five percent.

5. The method of claim 2 further comprising computing the A—A interval moving average from at least four A—A intervals.

6. The method of claim 2 further comprising limiting the value of an A—A interval used to compute the A—A interval moving average to a specified maximum value.

7. The method of claim 6 further comprising limiting the value of an A—A interval used to compute the A—A interval moving average to approximately 2000 milliseconds.

8. The method of claim 1 wherein the specified absolute value is approximately 600 milliseconds.

9. A cardiac rhythm management device, comprising:

an atrial sensing channel for detecting atrial events corresponding to atrial depolarizations;

a controller for measuring A—A intervals, where a present A—A interval is defined as the time interval between a presently detected atrial event and a previously detected atrial event, for computing a function based upon a plurality of measured A—A intervals, and for detecting a premature atrial contraction if the present A—A interval is less than the computed A—A interval function and wherein the present A—A interval must also be less than a specified absolute value in order for a premature atrial contraction to be detected.

10. The device of claim 9 wherein the computed A—A interval function is a moving average of present A—A intervals, and wherein the controller is programmed to detect a premature atrial contraction if the present A—A interval is less than a specified value based upon the A—A interval moving average.

11. The device of claim 10 wherein the specified value based upon the A—A interval moving average that the present A—A interval must be less than in order for a premature atrial contraction to be detected is a specified fraction of the A—A interval moving average.

12. The method of claim 11 wherein the specified fraction is approximately seventy-five percent of the moving average interval.

13. The device of claim 10 wherein the A—A interval moving average is computed from at least four A—A intervals.

14. The device of claim 10 wherein the value of an A—A interval used to compute the A—A interval moving average is limited to a specified maximum value.

15. The device of claim 14 wherein the value of an A—A interval used to compute the A—A interval moving average is limited to a specified maximum value of approximately 2000 milliseconds.

16. The device of claim 9 wherein the specified absolute value is approximately 600 milliseconds.

* * * * *

UNITED STATES PATENT AND TRADEMARK OFFICE
CERTIFICATE OF CORRECTION

PATENT NO. : 6,741,890 B1  
DATED : May 25, 2004  
INVENTOR(S) : Seim et al.

Page 1 of 1

It is certified that error appears in the above-identified patent and that said Letters Patent is hereby corrected as shown below:

Column 6,
Line 3, delete "method" and insert -- device --, therefor.

Signed and Sealed this

Fifth Day of April, 2005

JON W. DUDAS
*Director of the United States Patent and Trademark Office*